United States Patent [19]

Hoffman et al.

[11] Patent Number: 4,552,142
[45] Date of Patent: Nov. 12, 1985

[54] VENTILATOR SYSTEM HAVING A CONTROL VALVE IN THE VENTILATOR CIRCUIT

[75] Inventors: Allan Hoffman; Harry Benford, both of Toledo, Ohio

[73] Assignee: Ohio Medical Research, Inc., Toledo, Ohio

[21] Appl. No.: 608,704

[22] Filed: May 10, 1984

[51] Int. Cl.[4] .................................. A61M 25/00
[52] U.S. Cl. ............................ 128/207.16; 604/158
[58] Field of Search ................ 128/207.16, 207.15, 128/207.14, 204.25, 205.24, 200.26; 604/158

[56] References Cited

U.S. PATENT DOCUMENTS

| | | | |
|---|---|---|---|
| 1,176,146 | 3/1916 | Jones | 128/205.24 |
| 2,269,823 | 1/1942 | Kreiselman | 128/207.15 |
| 3,039,469 | 6/1962 | Fountain | 128/200.26 |
| 4,202,330 | 5/1980 | Jariabka | 128/205.24 |
| 4,416,273 | 11/1983 | Grimes | 128/207.15 |

FOREIGN PATENT DOCUMENTS 1296652  5/1962  France ..................... 128/207.16

*Primary Examiner*—Henry J. Recla
*Attorney, Agent, or Firm*—Fraser & Clemens

[57] ABSTRACT

The present invention relates to a ventilator system which utilizes a control valve to assist an attendant in disconnecting a ventilator conduit circuit from a patient's endotracheal tube. Prior to the present invention, when a ventilator system was operated in certain modes, disconnection of the endotracheal tube from the ventilator circuit caused water which may have accumulated in the ventilator circuit to spray over the patient and/or attendant. In the present invention, a control valve is connected between the outlet of the ventilator circuit and the patient's endotracheal tube. Normally, the valve is maintained in the open position to permit air to be supplied to the patient. However, when it is desired to disconnect the ventilator circuit from the patient's endotracheal tube, the control valve can be manually closed immediately prior to disconnecting the ventilator circuit, thereby preventing the spraying of any accumulated water.

5 Claims, 4 Drawing Figures

VENTILATOR SYSTEM HAVING A CONTROL VALVE IN THE VENTILATOR CIRCUIT

BACKGROUND OF THE INVENTION

The present invention relates generally to a ventilator system and, in particular, to a ventilator system which incorporates a control valve in the ventilator circuit.

Ventilator systems are widely utilized in hospitals in order to assist patients with respiratory problems in breathing. Typically, a ventilator system includes a ventilator unit which provides a supply of air containing a predetermined percentage of oxygen. The ventilator unit is provided with a heater and a humidifier for heating the air to a predetermined temperature having a desired amount of humidity. The ventilator system further includes a ventilator conduit circuit which comprises a plurality of flexible conduits utilized to supply the heated, humidified air to the patient. The air can be introduced into the patient's lungs by means of an endotracheal tube, for example.

The ventilator unit is typically provided with a plurality of controls for regulating the inspiration and expiration of the patient. In some instances, the ventilator system is operated in a mode wherein at least a portion of the ventilator circuit is maintained at a predetermined positive pressure with respect to atmospheric pressure. This particular mode is typically referred to as a positive end expiratory pressure (PEEP) mode.

Generally, the ventilator unit is set to heat the air to a temperature above a patient's body temperature such that, after the air has passed through the ventilator circuit and is ready to enter the patient, the air will have cooled to a temperature approximately equal to the patient's body temperature. This cooling of the air throughout the ventilator circuit causes condensation within the associated conduits and thus results in water collecting in the ventilator circuit. As a result of this condensation, it is necessary for hospital personnel to periodically inspect the ventilator circuit for water accumulation and, if necessary, drain the water from the ventilator circuit.

When it is desired to drain the accumulated water from a ventilator circuit, an attendant typically disconnects the outlet of the ventilator circuit from the patient's endotracheal tube. However, when the ventilator unit is operated in certain modes such as the above described PEEP mode, the pressurized air in the ventilator circuit causes the accumulated water to spray from the outlet of the ventilator circuit over the patient and/or attendant. While the spraying of the water can be prevented by turning down the PEEP control valve on the ventilator unit, this is often impractical due to the location of the ventilator unit relative to the patient and attendant.

SUMMARY OF THE INVENTION

The present invention concerns a control valve which is utilized in conjunction with a ventilator system to assist an attendant in disconnecting the ventilator circuit from the patient's endotracheal tube. In the preferred embodiment of the invention, the control valve is connected between the outlet of the ventilator circuit and the patient's endotracheal tube. Normally, the valve is maintained in the open position to permit air to be supplied to the patient. However, when it is desired to drain any accumulated water from the ventilator circuit, the control valve can be manually closed immediately prior to disconnecting the ventilator circuit from the endotracheal tube. This prevents any spraying of water from the ventilator circuit when the endotracheal tube is disconnected.

In the preferred embodiment of the invention, the control valve includes an actuator button which is spring bias to maintain the valve in the normally open position. The actuator button can be depressed by the operator to close the valve and, if desired, can be rotated to a locked position to maintain the valve in a closed position. Also, the valve includes means for locking the valve in an open position.

BRIEF DESCRIPTION OF THE DRAWINGS

The above, as well as other advantages of the present invention, will become readily apparent to one skilled in the art from reading the following detailed description in conjunction with the attached drawings in which.

DESCRIPTION OF THE PREFERRED EMBODIMENT

Figure 1:
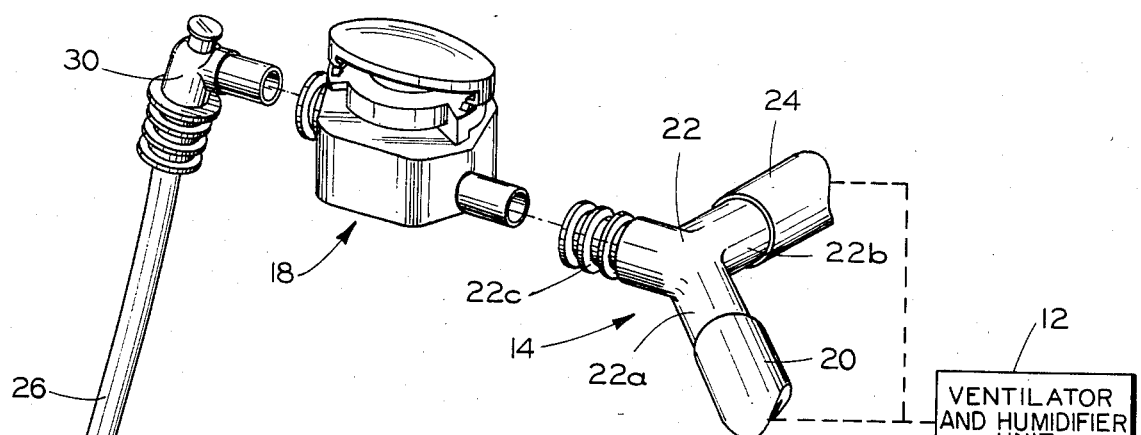
FIG. 1 is an exploded perspective view illustrating the individual components of the ventilator system of the present invention.

Referring to FIG. 1, there is shown an exploded perspective view illustrating a ventilator system 10 of the present invention. The system 10 includes a ventilator unit 12 which is connected to a ventilator conduit circuit 14. The connection between the ventilator unit 12 and the ventilator circuit 14 is represented by dashed lines 14a. The ventilator unit 12 and the ventilator conduit circuit 14 are adapted to supply air to a patient (not shown) through a suitable means such as an endotracheal tube 16. In accordance with the present invention, the ventilator circuit 14 is connected to the endotracheal tube 16 by means of a normally open control valve 18.

The conduit circuit 14 includes an inspiratory conduit 20 connected to a first connection point 22a of a "Y" connection 22, and an expiratory conduit 24 connected to a second connection point 22b of the "Y" connection 22. The third connection point 22c of the "Y" connection 22 is connected to the endotracheal tube 16 through the normally open control valve 18. The endotracheal tube 16 includes a tube member 26 having an inflatable cuff 28 at the lower end thereof which is adapted to be inserted into the trachea of the patient. The upper end of the tube 16 is connected to the valve 18 by means of a right angle connection 30. While the drawings illustrate an endotracheal tube for introducing air into the patient, it will be appreciated that other means could be utilized.

The control valve 18, which will be discussed in more detail hereinafter, can be manually closed by an attendant immediately prior to disconnecting the ventilator conduit circuit 14 from the endotracheal tube 16. Thus, when the ventilator 12 is operated in certain modes wherein the air supply in the ventilator circuit 14 is pressurized, the endotracheal tube 16 can be disconnected from the ventilator circuit 14 without causing any water which may have accumulated in the ventilator circuit 14 to spray over the patient and/or attendant.

It should be noted that the valve 18 illustrated in the drawings and described herein is only representative of one type of valve which can be utilized with the present invention. Preferably, the valve is spring biased to a normally open position and includes means for locking the valve in the open position to prevent any inadvertent closing of the valve by an attendant or a patient. The valve can also include means for locking the valve in a closed position during the disconnection and draining of the ventilator circuit.

While it is preferable to connect the valve between the outlet of the ventilator circuit and the patient's endotracheal tube, as shown in the drawings, it will be appreciated that that valve can also be connected in the inspiratory conduit 20. However, for reasons of convenience, it is preferable to locate the valve near the outlet end of the conduit 20.

Figure 2:
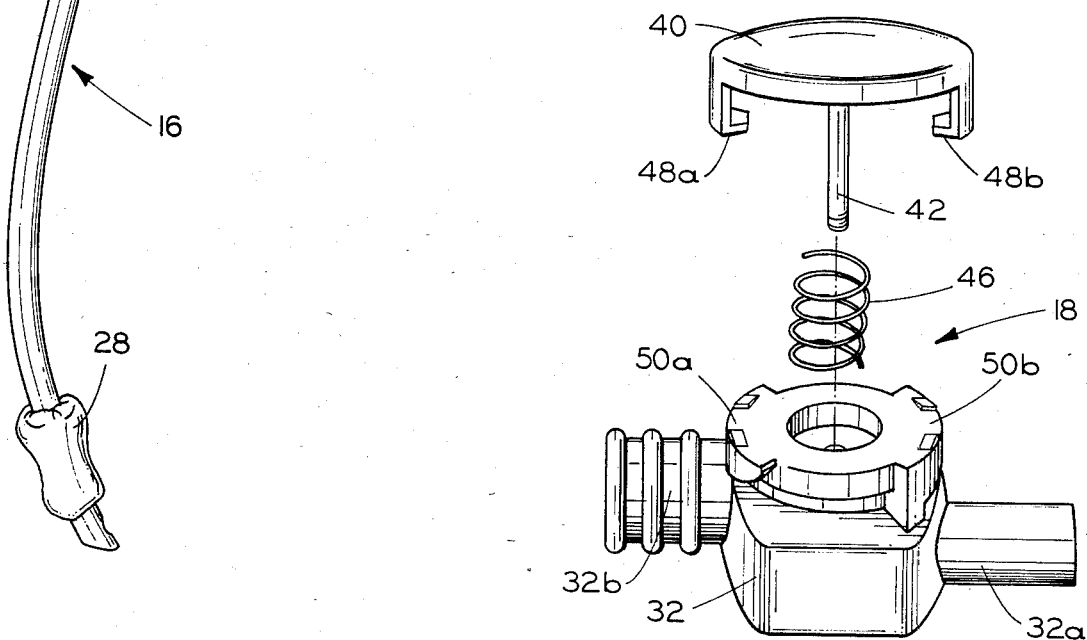
FIG. 2 is an exploded perspective view illustrating the individual components of a control valve utilized in the ventilator system of FIG. 1.
Figure 3:
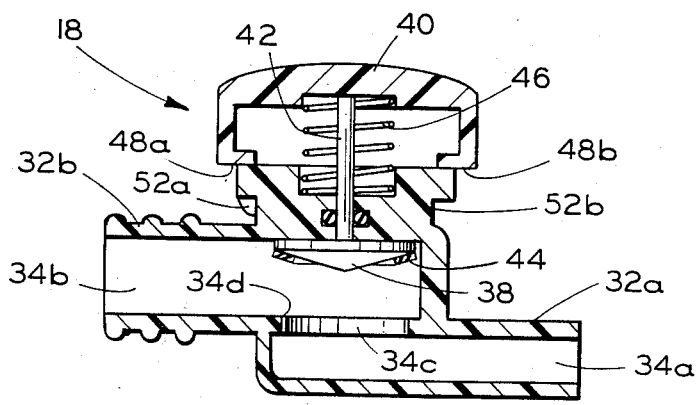
FIG. 3 is a sectional view of the control valve taken along line 3—3 of FIG. 1.
Figure 4:
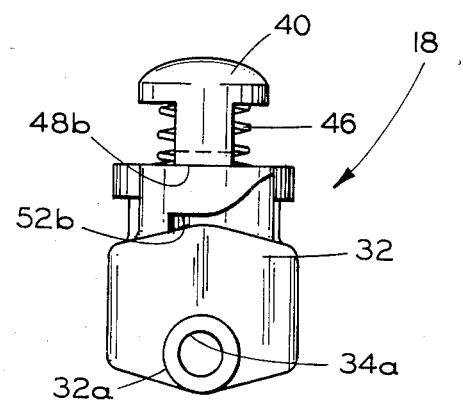
FIG. 4 is an end elevational view of the control valve illustrated in FIG. 3.

Referring to FIGS. 2 through 4, there is shown in more detail one type of normally open valve which can be utilized with the ventilator system of the present invention. The valve 18 includes a main body portion 32 having one end 32a adapted to be inserted within the "Y" connection point 22c and an opposite end 32b adapted to be connected to the patient's endotracheal tube 16. As shown in FIG. 3, the main body portion 32 of the valve includes a lower passageway 34a which communicates with an upper passageway 34b via a port 34c. An upper annular valve seat 34d surrounds the port 34c.

The valve 18 includes an actuating member 36 having a lower plug element 38 connected to an upper actuator button 40 by means of a stem 42 extending through an aperture formed in the main body 32. A resilient sealing ring 44 is secured to the lower surface of the plug element 38. The actuating member 36 is biased upperwardly by means of a spring 46 to maintain the valve 18 in a normally open position.

In order to lock the valve in a normally open position, the upper actuator button 40 is provided with diametrically opposed, downwardly extending tab members 48a and 48b which, when the valve is rotated to the position shown in FIG. 3, are received within recessed portions 50a and 50b formed in the upper face of the main body 32. In order to close the valve, the actuator button 40 is rotated approximately 90° from the position shown in FIG. 3, and is depressed downwardly to urge the resilient ring 44 into sealing engagement with the annular seat 34d, thereby closing the port 34c. The valve member 36 can be locked in the closed position by rotating the valve member 36 such that the lower tab members 48a and 48b are received within slots 52a and 52b formed in the main body 32. The slots 52a and 52b are each provided with an initial tapered portion to assist the attendant in moving the valve to the closed position.

In accordance with the provisions of the patent statutes, the principle and mode of operation of the invention have been illustrated and described in what is considered to represent its preferred embodiment. However, it should be understood that the invention may be practiced otherwise than as specifically illustrated and described without departing from its spirit or scope.

What is claimed is:

1. A ventilator system comprising, in combination:
   ventilator means for providing a supply of air at a predetermined pressure, said ventilator means including means for humidifying the pressurized air;
   conduit means having an inlet and an outlet, the inlet of said conduit means connected to said ventilator means to receive the pressurized and humidified air;
   tube means for introducing the pressurized and humidified air into a patient;
   normally open valve means connected between said tube means and the outlet of said conduit means for providing a normally open flow path therebetween, said valve means operable to close the outlet of said conduit means.

2. The ventilator system as defined in claim 1 wherein said normally open valve means includes means for locking said valves means in the normally open position.

3. The ventilator system as defined in claim 1 wherein said normally open valves means includes means for locking said valve means in the closed position.

4. The ventilator system as defined in claim 1 wherein said valve means includes biasing means for biasing said valve means to a normally open position.

5. The ventilator system as defined in claim 1 wherein said tube means is an endotracheal tube.

* * * * *